United States Patent [19]

Blanchard

[11] Patent Number: 4,599,609
[45] Date of Patent: Jul. 8, 1986

[54] PERSONAL LIQUID CHEMICAL AGENT DETECTOR

[75] Inventor: William C. Blanchard, Baltimore, Md.

[73] Assignee: Allied Corporation, Morristown, N.J.

[21] Appl. No.: 678,538

[22] Filed: Dec. 5, 1984

[51] Int. Cl.⁴ .................. G08B 21/00; G08B 17/10
[52] U.S. Cl. ........................ 342/602; 73/23; 324/65 R; 340/573; 340/632; 422/69; 422/55; 422/57; 436/150
[58] Field of Search ............ 340/514, 573, 602, 604, 340/632; 324/65 R; 73/23; 422/69; 436/150

[56] References Cited
U.S. PATENT DOCUMENTS

| 4,146,887 | 3/1979 | Magnante | 340/632 |
| 4,219,806 | 8/1980 | Enemark | 340/632 |
| 4,231,249 | 11/1980 | Zuckerman | 73/23 |
| 4,255,960 | 3/1981 | Boutonnat et al. | 340/632 X |
| 4,263,588 | 4/1981 | Gautier | 340/632 |
| 4,264,331 | 4/1981 | Klein et al. | 422/98 X |
| 4,297,689 | 10/1981 | Shaw et al. | 340/632 |
| 4,384,283 | 5/1983 | Drope et al. | 340/632 |
| 4,426,640 | 1/1984 | Becconsall et al. | 340/632 |
| 4,523,142 | 6/1985 | Murata et al. | 324/65 R |
| 4,549,427 | 10/1985 | Kolesar, Jr. | 73/23 |

Primary Examiner—James L. Rowland
Assistant Examiner—Daniel Myer
Attorney, Agent, or Firm—Robert M. Trepp; Bruce L. Lamb

[57] ABSTRACT

A personal liquid chemical agent detector incorporating a sensor which changes resistance in response to contact with liquid, first and second switches which function as pins for attaching the detector to the wearer and as electrical switches, a battery, a resistor, and a detector and alarm circuit. A conductor incorporating a resin, conductive flakes and dye crystals selected which are solvent in selected chemical agents. A conductive paint incorporating a resin, conductive flakes a dye solution including one or more volatile solvents and a plasticizer. The invention overcomes the problem of requiring additional switches for manual testing of the detector and battery prior to use and for disconnecting the battery after use at times the detector is removed by the wearer. The invention further overcomes the problem of independent verification of detection by providing a conductor with concurrent electrical and visual appearance responses to selected chemical agents absorbed by the conductor.

17 Claims, 6 Drawing Figures

PERSONAL LIQUID CHEMICAL AGENT DETECTOR

BACKGROUND OF THE INVENTION

1. Field of the Invention

This invention relates to liquid chemical agent detectors and more particularly to test provisions for a detector attached to the clothing worn by a person and to a paint and a conductor for use in detectors for detecting selected chemical agents.

2. Description of the Prior Art

In the past, difficulties have arisen from the use of small devices, such as a radio pager, which are attached to the clothing worn by a person. When the device is attached to the clothing worn by a person, the device must be turned on or activated and when the device is removed from the person, the device must be turned off. Typically, the device has a battery which will be discharged, if not turned off when not in use. A further problem is to test the device to assure its proper operation after long periods of storage prior to use and periodically during the life of the device. Prior devices included switches and knobs which are switched or turned in a predetermined sequence to turn on and test the device.

In the prior art, certain non-electric liquid chemical agent detectors included paper impregnated or covered with certain chemicals which, when exposed to certain chemical agents, exhibited a change in color of the paper in the region wetted. The paper coated with predetermined chemicals provided a visual indication of certain desired chemical agents, such as: GB, GD, VX and HD. The paper was supplied by Knowlton Brothers identified by National Stock No. 6665-00-050-8529.

It is therefore desirable to provide a personal liquid agent detector which does not require switches or knobs to activate the detector when a user attaches it to his clothing.

It is further desirable to provide a liquid chemical agent detector which includes means for testing the detector prior to use by engaging and opening switches which also serve to attach the detector to personal clothing.

It is further desirable to provide a personal liquid chemical agent detector having a battery which, when attached to clothing, is operating i.e. the battery is connected, and when detached from personal clothing, the detector is deactivated i.e. by opening the battery circuit.

It is further desirable to provide a personal liquid chemical agent detector providing both electrical and visual means for indicating the presence of certain chemical agents.

It is further desirable to provide a conductor which is formulated to respond to the presence of a chemical agent by a change in its electrical resistance and by a change in its appearance, for example its color.

It is further desirable to provide a conductor having a predetermined solubility constant to match certain chemical agents which will be readily absorbed by the conductor causing the conductor to swell, wherein conductive particles within the conductor are separated from one another by the swelling.

It is further desirable to provide a conductor having certain chemical crystals therein, which when wetted by a certain chemical agent or agents is dissolved into the liquid whereby the appearance of the liquid is changed, for example in color.

SUMMARY OF THE INVENTION

A detector for detecting a liquid comprising a sensor including a conductor of predetermined material having a first and second end, the material of the conductor selected to react with the liquid at times the liquid is in contact with the conductor whereby the resistance of the conductor is changed, first and second switches each having a long pin and a receiver for receiving an end of the pin when the switch is closed, means to hold the long pin away from the receiver when the switch is open, and means for making electrical connection to the long pin and to the receiver, respectively, a battery having a first and second terminal, the first terminal coupled through the first switch to the first end of the sensor, the second terminal coupled through a resistor and the second switch to the second end of the sensor, the common junction of the resistor and the second switch also coupled to a circuit for detecting a predetermined change in the resistance of the conductor and for providing an alarm at times the first and second switch are closed and for testing the circuit at times the first switch is closed and the second switch is open.

The invention further provides a method for testing a personal liquid chemical agent detector, wherein the detector is held to personal clothing by first and second pins, also functioning as first and second electrical switches, respectively, the first switch coupled between one side of a sensor and one side of a battery and the second switch coupled between the other side of the sensor and a detector and alarm circuit, as well as a resistor and a second side of the battery comprising the steps of fastening the first switch to cause the alarm circuit to alarm, opening the first switch to cause the alarm to deactivate, fastening the second switch, fastening the first switch to activate the sensor.

The invention further provides a conductive paint for a liquid chemical agent detector comprising a resin having a predetermined solubility constant after said paint is cured, a plurality of conductive flakes, a dye solution dissolved in one or more volatile solvents, the dye solution forming crystals when the solvents are evaporated, the dye crystals selected to be solvent in one or more selected chemical agents, and a plasticizer; the resin, plurality of conductive flakes, dye solution and plasticizer mixed together to form the paint.

The invention further provides a conductor for a liquid agent chemical detector comprising a resin having a predetermined solubility constant, the resin including a mixture of conductive flakes to provide a predetermined conductivity and dye crystals selected to be solvent in one or more selected chemical agents.

DESCRIPTION OF THE PREFERRED EMBODIMENT

Figure 1:
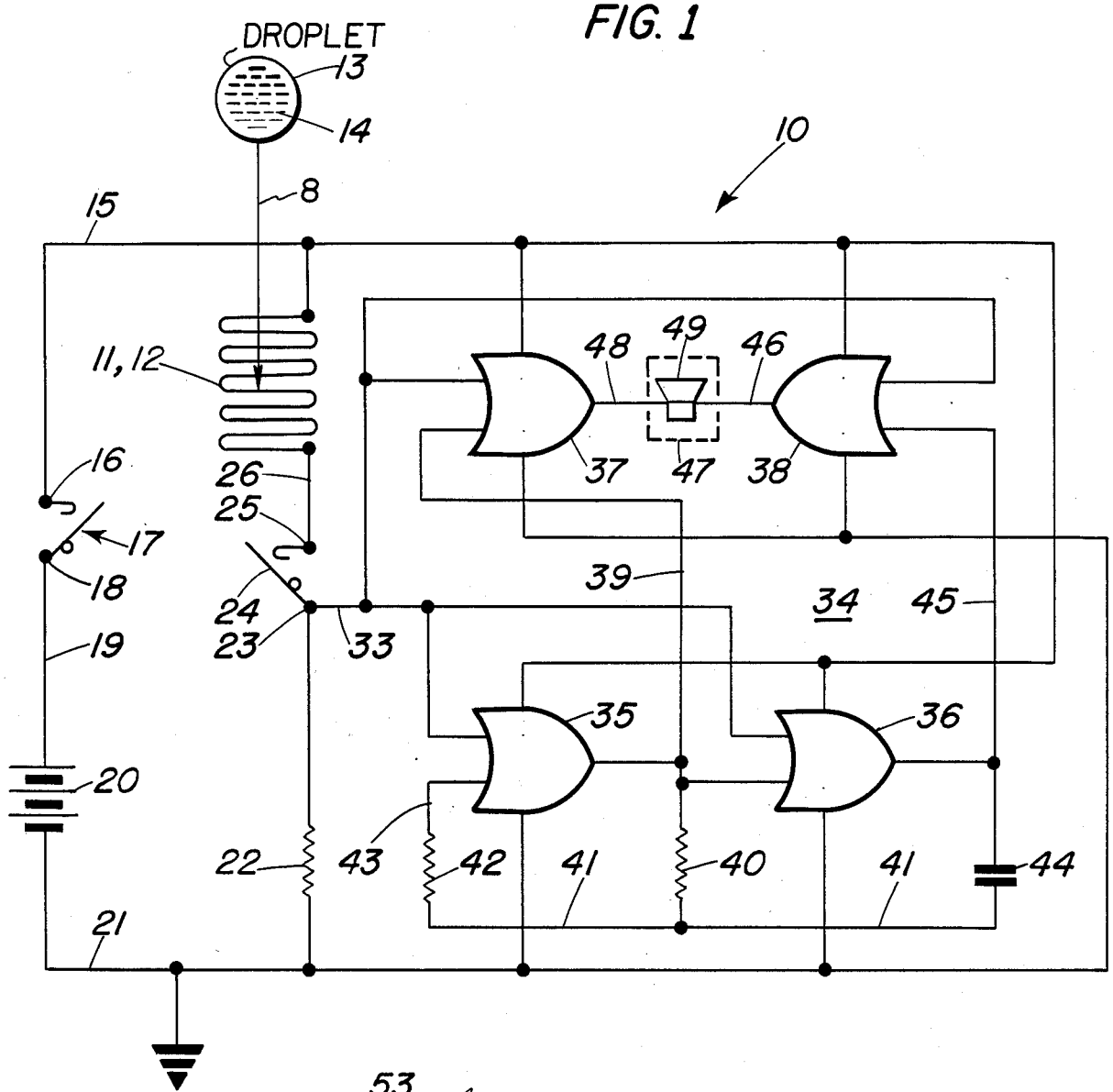
FIG. 1 is a schematic diagram of one embodiment of the invention.

Referring to FIG. 1, a schematic diagram of a liquid agent detector 10 is shown. A sensor 11 has a conductor 12 of predetermined material selected to physically or chemically react with a liquid 14, such as in droplet 13, at times droplet 13 is in contact with conductor 12 by following arrow 8, for example. Liquid 14 and droplet 13 may, for example, be absorbed into conductor 12 to cause the resistance of conductor 12 to increase. Conductor 12 may swell or enlarge as a result of absorbing droplet 13 causing conductive flakes or particles therein to separate. Sensor 11 is coupled over line 15 to terminal 16 of switch 17. Terminal 18 of switch 17 is coupled over line 19 to the positive side of battery 20 or other power source, such as solar cells. Switch 17 may be a single pole, single throw switch. The negative side of battery 20 is coupled over line 21 through resistor 22 to terminal 23 of switch 24. Switch 24 is a single pole, single throw switch having terminal 25 coupled over line 26 to the other side of sensor 11. Terminal 23 of switch 24 is also coupled over line 33 to an input of detector and alarm circuit 34. Line 33 is coupled to an input of OR gates 35 through 38. The output of OR gate 35 is coupled over line 39 to a second input of OR gates 36 and 37 and through resistor 40 over line 41 through resistor 42 and over line 43 to a second input of OR gate 35. Line 41 is also coupled through capacitor 44 and over line 45 to the output of OR gate 36 and a second input of OR gate 38. The output of OR gate 38 is coupled over line 46 to one side of alarm 47 which may be, for example, an alarm to alert a person such as a visual or audible alarm, for example, a piezoelectric horn 49. The output of OR gate 37 is coupled over line 48 to the other side of alarm 47. OR gates 37 and 38 function to provide a push-pull potential across alarm 47. An audible alarm may have, for example, a tone with an intensity of 80 decibels at 30 cm away from the detector at a frequency of about 2.8 Khz. The power supply for detector and alarm circuit 34 is coupled from battery 20 over line 19 through switch 17 over line 15 to the power supply connection of OR gates 35-38. The ground side of OR gates 35-38 are coupled over line 21 to battery 20.

In operation, switches 17 and 24 are initially closed. Sensor 11 has a predetermined resistance and upon contact with liquid 14, the resistance of sensor 11 increases above the resistance of resistor 22 to cause the potential on line 33 to decrease, causing OR gates 35 and 36 to oscillate. The oscillating frequency is determined by the value of capacitor 44 and resistances 40 and 42. The output of OR gates 35 and 36 are coupled to OR gates 37 and 38 which provide a push-pull drive to alarm 47.

Battery 20 provides the electrical current through sensor 11 and resistor 22. The resistance of sensor 11 is much less than the resistance of resistor 22 and the potential on line 33 is high. If no droplets 13 of liquid 14 are in contact with sensor 11, then sensor 11 will maintain its initial low resistance which will provide a predetermined potential on line 33, depending on the value of resistor 22 and the voltage of battery 20 and the output of OR gates 35 and 36 will be high.

Switches 17 and 24 provide a means for performing tests on detector 10 and at the same time provide a means for attaching detector 10 to personal clothing worn by a person. Detector 10 may initially be stored for a long period of time, months, for example, prior to use by a person. The detector may be tested by engaging switch 17 while leaving switch 24 open. The potential on line 33 will be low, since switch 24 is open. This condition of low potential on line 33 coincides with a high resistance of sensor 11 which occurs at time sensor 11 is in contact with liquid 14. Detector and alarm circuit 34 will activate, generating an audible alarm from alarm 47. Switch 17 may now be opened, causing power to be removed from OR gates 35-38. Switch 24 may then be closed, coupling sensor 11 to line 33. Switch 17 may then be reclosed, causing power on line 15 to be coupled to OR gates 35-38 and causing a current through sensor 11 and resistor 22. If sensor 11 has a predetermined low resistance, such as one that has not been in contact with liquid 14, the potential on line 33 will be of a predetermined value to cause OR gates 35 and 36 not to oscillate. The sensor is now operating and at times when liquid 14 is in contact with sensor 11, the resistance of sensor 11 will increase, causing alarm 47 to be energized. When the wearer of personal liquid chemical agent detector 10 removes detector 10 from an outer garment, such as at the end of a day, both switches 17 and 24 will be open, causing battery 20 to be electrically isolated from sensor 11 and from detector and alarm circuit 34.

Figure 2:
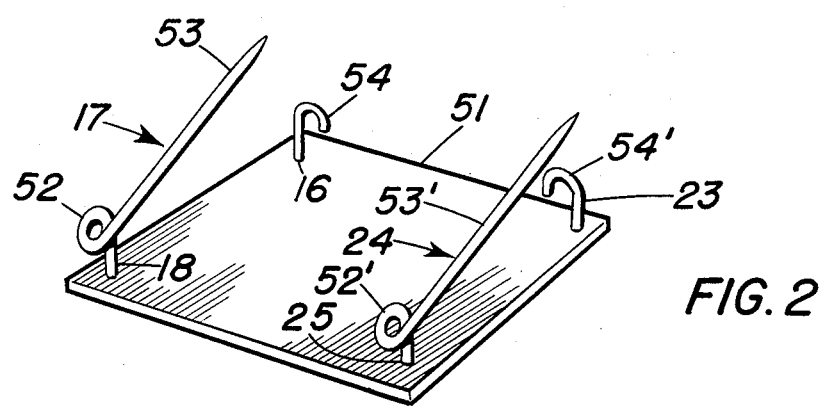
FIG. 2 is a view of one embodiment of switches suitable for use in FIGS. 1 and 3.

FIG. 2 is a view of switches 17 and 24 which are constructed in a manner suitable for affixing the detector to clothing at times switches 17 and 24 are closed, such as part of a safety pin. As may be seen in FIG. 2, terminals 18 and 16 are staked to a printed circuit board 51. Switch 17 has a loop or loops of wire 52 coupled to terminal 18 which is extended to form a pin or arm 53. Terminal 16 has a receiver or metal hook 54 staked to printed circuit board 51. Arm or pin 53 may be flexed by means of loop 52 to be positioned underneath receiver or metal hook 54. Terminals 18 and 16 are spaced apart a suitable distance, such as one-half to two inches to facilitate closing and opening switch 17 with a person's thumb and fingers. When switch 17 is closed, loop 52 provides a force on pin or arm 53 to hold pin 53 securely in hook 54. At times switch 17 is open, loop 52 provides a force on pin 53 to move pin 53 away from and out of contact with hook 54. Switches 17 and 24 may each be implemented with strips of conductive flexible material having a conductive fastener, such as snaps, belt buckles or Velcro.

Figure 3:
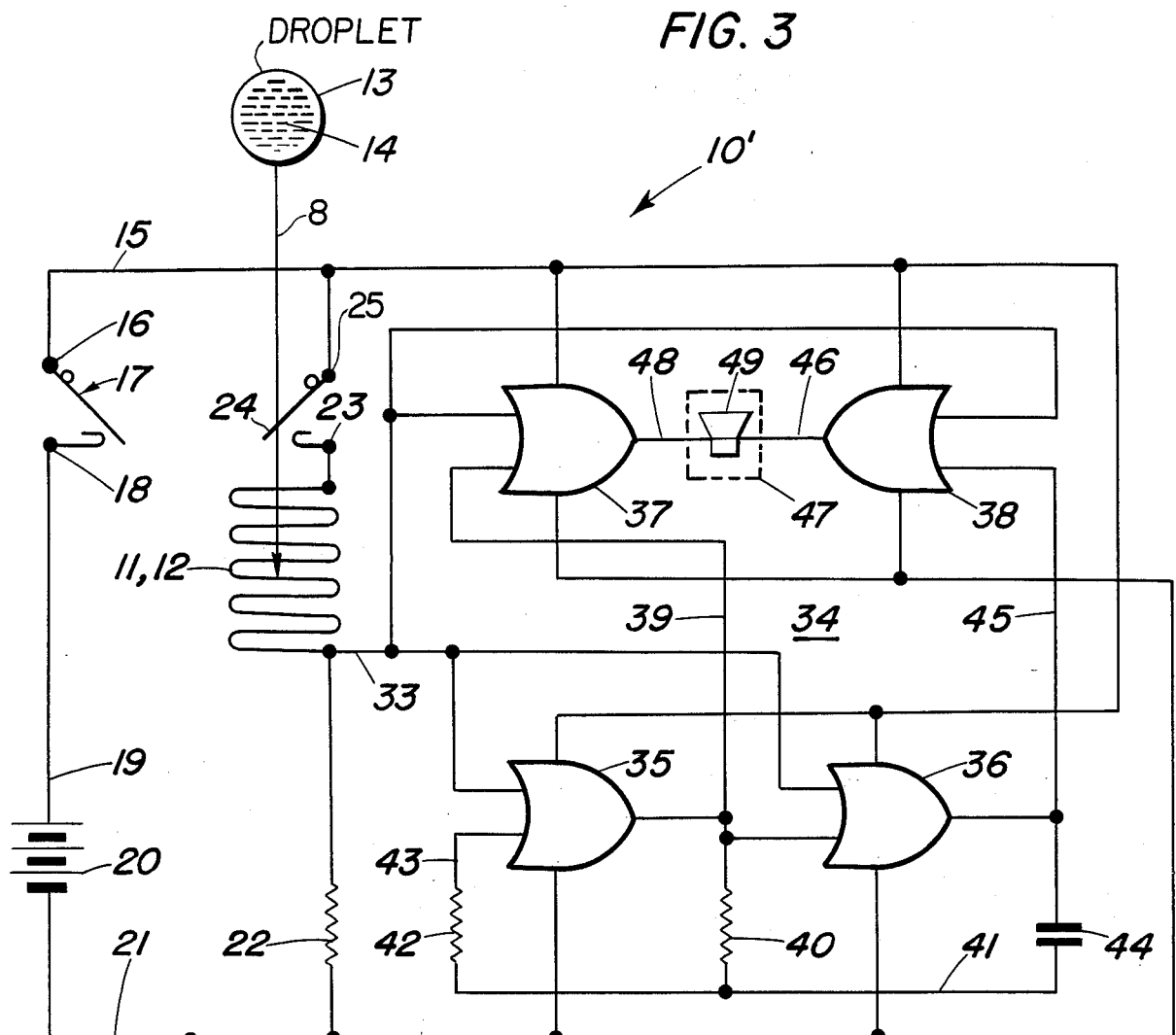
FIG. 3 is a schematic diagram of an alternate embodiment of the invention.

FIG. 3 is a schematic diagram of an alternate embodiment of the invention. In FIG. 3, like references are used for functions corresponding to the apparatus of FIG. 1. Referring to FIG. 3, the position of sensor 11 and switch 24 have been interchanged with respect to FIG. 1. Switches 17 and 24 have terminals 16 and 25 coupled together over line 15. Terminals 16 and 25 of switches 17 and 24 may be coupled to pins or arms 53 and 53' shown in FIG. 2. Thus, if pins or arms 53 and 53' of switches 17 and 24 come in contact inadvertently while switches 17 and 24 are open, no current will flow through or bypass either switch.

Figure 4:
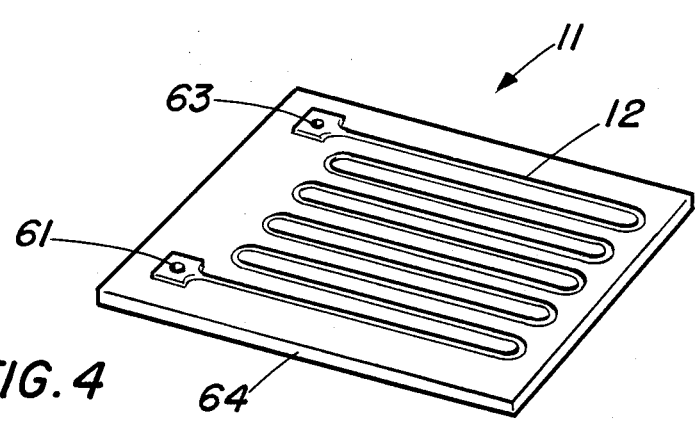
FIG. 4 is a perspective view of a sensor suitable for use in the embodiments shown in FIGS. 1 and 3.

FIG. 4 shows a perspective view of one embodiment of sensor 11. In FIG. 4 a conductor 12 winds back and forth in a serpentine pattern between terminals 61 and 63. Conductor 12 has a predetermined width, such as in the range from 150 to 200 microns and a predetermined spacing in the range from 150 to 200 microns. The conductor width and spacing are suitable for detecting a single 200 micron droplet of a chemical agent such as GB, GD, VX, or HD.

GB has the following chemical name and synonyms:
Phosphonofluoridic acid, methyl-, isopropyl ester; Phosphonofluoridic acid, methyl-, 1-methylethyl ester and may have the chemical formula $C_4H_{10}FO_2P$, which is a Fluorinated organophosphorus compound.

GD has the following chemical name and synonyms:
Phosphonofluoridic acid, methyl-1,2,2-trimethylpropyl ester and may have the chemical formula $C_7H_{16}FO_2P$, which is a Fluorinated organophosphorus compound.

VX has the following chemical name and synonyms:
Phosphonothioic acid, methyl-, S-(2-bis(1-methylethylamino) ethyl)0-ethyl ester
O-ethyl S-(2-diisopropylaminoethyl)methyl phosphonothioate
S-2-Diisopropylaminoethyl O-ethyl methylphosphonothioate
S-(2-(Diisopropylamino)ethyl)O-ethylmethylphosphonothiolate
O-ethyl S-(2-diisoproplyaminoethyl)methylphosphonothioate
O-ethyl S-(2-diisoproplyaminoethyl)methylthiophosphonoate
and may have the chemical formula $C_{11}H_{26}NO_2PS$, which is a sulfinated organophosphorus compound.

HD has the following chemical name and synonyms:
Ethane, 1,1'-thiobis(2-chloro-)
Sulfide, bis(2-chloroethyl)
Bis(beta-chloroethyl)sulfide
Bis(2-chloroethyl)sulfide
1-chloro-2-(beta-chloroethylthio)ethane
beta,beta'-dichlorodiethyl sulfide
2,2'-dichlorodiethyl sulfide
Di-2-chloroethyl sulfide
beta,beta'-dichloroethyl sulfide
2,2'-dichloroethyl sulfide
and may have the chemical formula $c_4H_8Cl_2S$, which is a chlorinated sulfur compound.

Conductor 12 is supported by substrate 64 which may be, for example, ceramic, glass, plastic, printed circuit board material, metal with a non-conductive coating or other semi-rigid material for supporting the paint.

Figure 5:
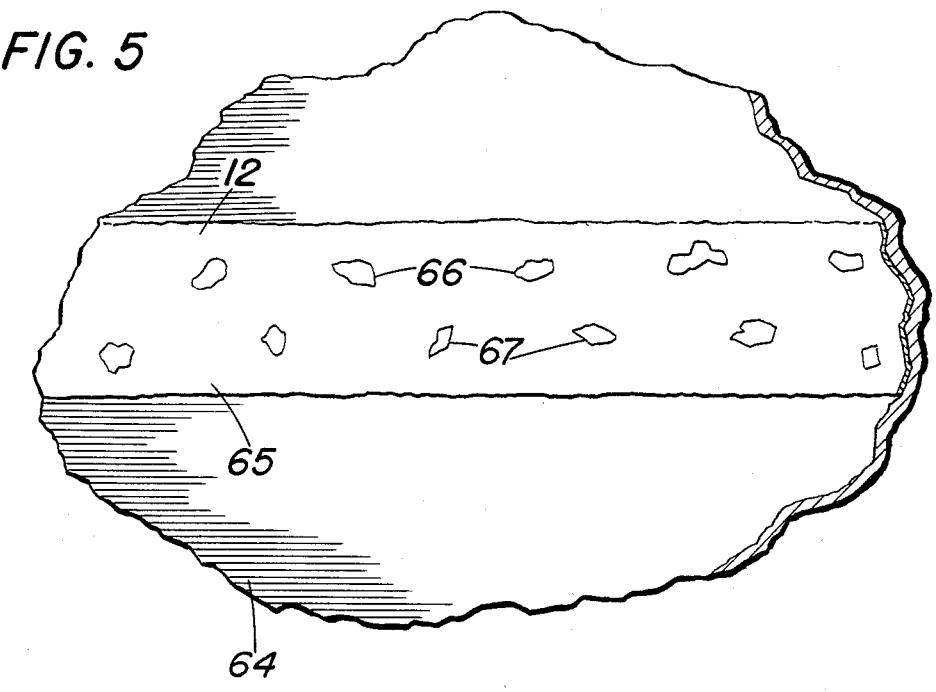
FIG. 5 is an enlarged view of one embodiment of a conductor.

Referring to FIG. 5, conductor 12 may be a resin 65 having a predetermined solubility constant. The solubility constant is selected to match the solubility constant of the chemical agent desired to be detected to optimize absorption of the chemical agent. The resin 65 may include silver flakes or particles 66 and dye crystals 67 mixed together. Dye crystals 67 are selected to be solvent in the desired liquid agent to be detected. The dye crystals when dissolved in the liquid agent provide a change of appearance of the liquid agent or conductor by the color of the dye which provides a visual indication of the presence of a particular liquid agent.

One example of a dye crystal to provide a green color when dissolved by certain chemical agents is Ethyl-bis-(2,4 Dinitrophenyl)acetate. One example of a dye crystal for providing the color yellow when dissolved in certain chemical agents is Thiodiphenyl-4, 4[1] diazo-bis-salicylic acid. One example of a dye crystal which, when dissolved in certain chemical agents will exhibit a red is 2,5:2[1], 5[1] Tetramethyl-triphenylmethane 4, 4[1] diazo-bis-beta hydroxynaphthoic anilide.

Conductor 12 may be formed, for example, from a paint which may be silk screened on or transferred onto substrate 64 and cured. The conductive paint may comprise, for example, a resin 65 having a predetermined solubility constant after the paint is cured, a plurality of conductive particles or silver flakes 66 to provide a predetermined conductivity after the paint is cured, a dye solution dissolved in one or more volatile solvents, and a plasticizer. The paint is made by mixing together the resin, plurality of silver flakes, dye solution and plasticizer. The dye solution forms dye crystals 67 when the solvents are evaporated. The dye crystals 67 are selected to be solvent in one or more of the selected chemical agents.

Conductor 12 reacts with the chemical agent to provide a change in resistivity of conductor 12, such as by absorption of the chemical agent causing conductor 12 or resin 65 to swell or expand, separating the silver flakes, thereby increasing the resistivity. At the same time conductor 12 absorbs the selected chemical agent having a solubility constant which matches the solubility of the conductor, the chemical agent dissolves dye crystals 67 causing a change in appearance of conductor 12, such as by a predetermined color indicative of a certain chemical agent. Conductor 12 therefore provides two independent means at the same location for indicating the presence of a certain chemical agent arising from a single chemical agent droplet which may be a 200 micron in diameter droplet. The visual and electrical confirmation of the existence of the chemical agent enhances the confidence level and specificity of the liquid agent detector.

The resin may be, for example, silicon polyester resin. The resin may be an acrylic paint, for example. One example of a plasticizer is triacetin glycerl triacetate. The solvents for the dyes may be, for example, ethoxy ethanol acetate and two different alcohols. The dyes may be solvent when mixed with the resin. Upon curing of the paint, the dyes will recrystalize and be spaced apart in the resin. The recrystalized dyes may, for example, be dull in color. When the dyes are redissolved in a chemical agent, the appearance of the conductor 12 will change.

Figure 6:
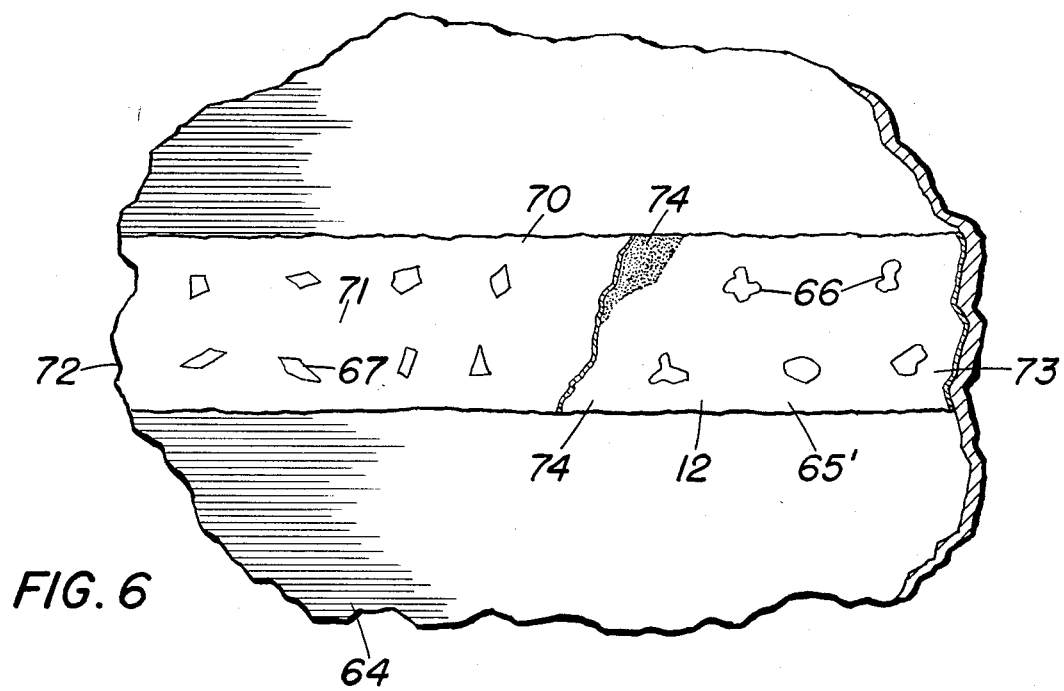
FIG. 6 is an enlarged view of an alternate embodiment of a conductor.

In an alternate embodiment shown in FIG. 6, a layer 70 of dye crystals 67 may be formed over conductor 12. In FIG. 6, like references are used for functions corresponding to the apparatus of FIG. 5. The resin 65 may include silver flakes or conductive particles 66. Resin 65 may be positioned along a path 71 between a first end 72 and a second end 73 on substrate 64. Other materials suitable for particles 66 include gold, platinum, copper, nickel, or other metals and combinations thereof. Layer 70 may be formed by dusting conductor 12 with crystals 67 while the surface 34 of conductor 12 is sticky prior to complete curing. Alternatively, a layer of material 74 functioning as a glue or adhesive may be deposited on surface 74 of conductor 12 prior to dusting with dye crystals 67. Material 74 would be sticky at the time of dusting to hold dye crystals 67 firmly in place after setting. With layer 70 on the surface of conductor 12 or on material 74, the concentration of dye crystals 67 is greater in the region visible to an observer without the need for mixing dye crystals 67 throughout conductor 12 prior to curing.

A personal liquid agent detector has been described including means for testing the detector by the wearer of the detector and means for connecting and disconnecting the battery at times the detector is attached or removed from the clothing of the wearer.

The personal liquid agent detector further includes a sensor having a conductor which, in response to receiving certain chemical agents, such as a 200 micron droplet provides a change in resistivity of the conductor and a change in the visual appearance of the conductor due to the presence of dye crystals.

The invention claimed is:

1. A detector for detecting a liquid wherein the detector is attached to clothing of the wearer comprising
   a sensor including a conductor of predetermined material having a first and second end, said predetermined material selected to react with said liquid at times said liquid is in contact with said conductor, whereby the resistance of said conductor is changed,
   first and second electrical switches having means for attaching said detector to said clothing,
   a battery having a first and second terminal, said first terminal coupled through said first switch to said first end of said sensor, said second terminal coupled through a resistor and said second switch to said second end of said sensor,
   said common junction of said resistor and said second switch also coupled to a circuit for detecting a predetermined change in said resistance of said conductor and for providing an alarm at times said first and second switch are closed and for testing said circuit at times said first switch is closed and said second switch is open.

2. The detector according to claim 1 wherein said means for attaching includes
   a pin and a receiver for receiving one end of said pin to close said switch,
   and means to hold said pin away from said receiver at time when said switch is open, means for making electrical connection to said pin and to said receiver, respectively.

3. The detector according to claim 2 wherein said means to hold said pin away includes a loop of wire.

4. The detector according to claim 2 wherein said pin has one end staked to a printed circuit board and said receiver is staked to said printed circuit board.

5. The detector according to claim 2 wherein said first and second switches are spaced apart to permit manual operation of each pin independent of the other.

6. The detector according to claim 1 further including a case for holding said sensor exposed to the environment, said first and second electrical switches, said battery, said resistor and said circuit, said means for attaching said detector to said clothing extending through said case beyond the exterior surface of said case.

7. The detector according to claim 1 wherein said circuit has a power supply terminal coupled through said first switch to said first terminal of said battery.

8. The detector according to claim 7 wherein said circuit has a ground supply terminal coupled to said second terminal of said battery.

9. A detector for detecting a liquid wherein the detector is attached to clothing of the wearer comprising
   a sensor including a conductor of predetermined material having a first and second end, said predetermined material selected to react with said liquid at times said liquid is in contact with said conductor, whereby the resistance of said conductor is changed,
   first and second electrical switches having means for attaching said detector to said clothing,
   a battery having a first and second terminal, said first terminal coupled through said first and second switches to said first end of said sensor, said second terminal coupled through a resistor to said second end of said sensor,
   said common junction of said resistor and said second end of said sensor also coupled to a circuit for detecting a predetermined change in said resistance of said conductor and for providing an alarm at times said first and second switches are closed and for testing said circuit at times said first switch is closed and said second switch is open.

10. The detector according to claim 9 wherein said means for attaching includes
    a pin and a receiver for receiving one end of said pin to close said switch,
    and means to hold said pin away from said receiver at time when said switch is open, means for making electrical connection to said pin and to said receiver, respectively.

11. The detector according to claim 10 wherein said means to hold said pin away includes a loop of wire.

12. The detector according to claim 10 wherein said pin has one end staked to a printed circuit board and said receiver is staked to said printed circuit board.

13. The detector according to claim 10 wherein said first and second switches are spaced apart to permit manual operation of each pin independent of the other.

14. The detector according to claim 9 further including a case for holding said sensor exposed to the environment, said first and second electrical switches, said battery, said resistor and said circuit, said means for attaching said detector to said clothing extending through said case beyond the exterior surface of said case.

15. The detector according to claim 9 wherein said circuit has a power supply terminal coupled through said first switch to said first terminal of said battery.

16. The detector according to claim 15 wherein said circuit has a ground supply terminal coupled to said second terminal of said battery.

17. A method for testing a personal detector for detecting a liquid where said detector is held to personal clothing by first and second pins also functioning as first and second electrical switches respectively, the first switch coupled between one side of a sensor and one side of a battery and the second switch coupled between the other side of the sensor and a detector and alarm circuit as well as a resistor and a second side of said battery comprising the steps of:
    fastening said first switch to cause said alarm circuit to alarm, opening said first switch to cause the alarm to deactivate, fastening said second switch, fastening said first switch to activate said sensor.

* * * * *